United States Patent
Abramovici et al.

(10) Patent No.: US 9,018,250 B2
(45) Date of Patent: Apr. 28, 2015

(54) PHARMACEUTICAL COMPOSITION AND DOSAGE FORM COMPRISING DRONEDARONE, AND PREPARATION METHOD THEREOF

(71) Applicant: Sanofi, Paris (FR)

(72) Inventors: Bernard Abramovici, Juvignac (FR); Stephane Beilles, Montpellier (FR); Sandra Chambonnet, Clapiers (FR); Jean-Claude Gautier, Clapiers (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/887,562

(22) Filed: May 6, 2013

(65) Prior Publication Data
US 2013/0245115 A1  Sep. 19, 2013

Related U.S. Application Data

(63) Continuation of application No. PCT/FR2011/052622, filed on Nov. 10, 2011.

(30) Foreign Application Priority Data

Nov. 10, 2010 (FR) ..................... 10 59306

(51) Int. Cl.
*A61K 31/34* (2006.01)
*A61K 31/343* (2006.01)
*A61K 9/48* (2006.01)

(52) U.S. Cl.
CPC ............ *A61K 31/343* (2013.01); *A61K 9/4858* (2013.01); *A61K 9/4866* (2013.01); *Y10S 514/96* (2013.01)

(58) Field of Classification Search
USPC ......................................... 514/469
See application file for complete search history.

(56) References Cited

U.S. PATENT DOCUMENTS

| | | |
|---|---|---|
| 3,248,401 A | 4/1966 | Tondeur |
| 5,100,911 A | 3/1992 | Binder et al. |
| 5,223,510 A | 6/1993 | Gubin et al. |
| 6,949,583 B2 | 9/2005 | Assens et al. |
| 7,323,493 B1 * | 1/2008 | Abramovici et al. ......... 514/469 |
| 8,318,800 B2 * | 11/2012 | Abramovici et al. ......... 514/469 |
| 2008/0139645 A1 * | 6/2008 | Abramovici et al. ......... 514/469 |
| 2013/0116316 A1 | 5/2013 | Abramovici et al. |

FOREIGN PATENT DOCUMENTS

| | | |
|---|---|---|
| CN | 102188417 | 9/2011 |
| EP | 0338746 | 10/1989 |
| EP | 1315709 | 6/2003 |
| FR | 2764800 | 12/1998 |
| WO | WO 88/07996 | 10/1988 |
| WO | WO 89/02892 | 4/1989 |
| WO | WO 90/02743 | 3/1990 |
| WO | WO 94/29289 | 12/1994 |
| WO | WO 02/45693 | 6/2002 |
| WO | WO 2005/048979 | 6/2005 |
| WO | WO 2008/063323 | 5/2008 |
| WO | WO 2011/113320 | 9/2011 |
| WO | WO 2011113320 A1 * | 9/2011 |

OTHER PUBLICATIONS

Australian Public Assessment Report for Dronedarone Hydrochloride. Published Oct. 2010.*
Kerwin, B.A., et al., Journal of Pharmaceutical Sciences, vol. 97, pp. 2924-2935. Published 2008.*
Schick, M.J. et al., Nonionic surfactants physical chemistry. Published 1987.*
Tween 80 MSDS product page. Published 2005.*
Chambin, O., et al., Drug Development and Industrial Pharmacy vol. 31 pp. 527-534, published 2005.*
(Australian Public Assessment Report for Dronedarone HCl, published Oct. 2010).*
International Search Report for WO2012/063005 dated May 18, 2012.

* cited by examiner

*Primary Examiner* — Paul Zarek
*Assistant Examiner* — George W Kosturko
(74) *Attorney, Agent, or Firm* — Kelly L. Bender

(57) ABSTRACT

The disclosure relates to a pharmaceutical composition for oral administration, containing, as active principle, a benzofuran derivative having antiarrhythmic activity, in particular dronedarone and the pharmaceutically acceptable salts thereof, and at least one lipid carrier, said pharmaceutical composition being intended to be used in unit dosage form of the capsule type, in particular with a hard shell. This pharmaceutical composition and the dosage form comprising such a composition aim to limit the meal time effect following oral administration in humans. The lipid carrier allows: the solubilization of the active principle of the invention; and the shielding thereof from the negative effects of pH in the intestinal tract, thereby allowing same to be spared from the meal effect to a significant extent.

21 Claims, 7 Drawing Sheets

PHARMACEUTICAL COMPOSITION AND DOSAGE FORM COMPRISING DRONEDARONE, AND PREPARATION METHOD THEREOF

This application is a continuation of International Application No. PCT/FR2011/052622, filed Nov. 10, 2011, which is incorporated herein by reference in its entirety; which claims the benefit of priority of French Patent Application No. 1059306, filed Nov. 10, 2010.

The present invention generally relates to a pharmaceutical composition for oral administration containing an active principle with antiarrhythmic activity. More precisely, the invention relates to a semi-solid or liquid pharmaceutical composition intended to be used advantageously in a dosage form of the capsule type, said composition comprising at least one benzofuran derivative, as active principle, with antiarrhythmic activity and at least one lipid excipient.

The present invention also relates to a method of preparing a dosage form of this kind based on said pharmaceutical composition and also relates to the therapeutic application of said composition or of said dosage form.

"Benzofuran derivative with antiarrhythmic activity" denotes, in the context of the present invention, a benzofuran compound selected from those described in U.S. Pat. No. 3,248,401, U.S. Pat. No. 5,223,510 and EP 338746 as well as in patent applications WO 88/07996, WO 89/02892, WO 90/02743 and WO 94/29289.

Among these compounds, we may mention, 2-n-butyl-3-[4-(3-di-n-butylaminopropoxy)benzoyl]-5-methylsulfonamidobenzofuran or dronedarone and the pharmaceutically acceptable salts thereof described in patent EP1315709 as well as 2-n-butyl-3-(3,5-diiodo-4-diethylaminoethoxybenzoyl)benzofuran or amiodarone and the pharmaceutically acceptable salts thereof described in U.S. Pat. No. 3,248,401.

Advantageously, the benzofuran derivative with antiarrhythmic activity is selected from dronedarone or 2-n-butyl-3-[4-(3-di-n-butylaminopropoxy)benzoyl]-5-methylsulfonamidobenzofuran of formula (D) in the form of free base shown below and its derivatives, such as pharmaceutically acceptable salts described hereunder.

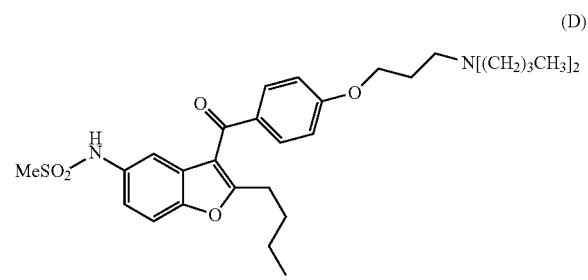

(D)

"Pharmaceutically acceptable salt" means a salt which is not toxic to the individual to whom it is administered when it is administered at standard doses. Thus, as pharmaceutically acceptable salts of dronedarone we may mention for example 2-n-butyl-3-[4-(3-di-n-butylaminopropoxy)benzoyl]-5-methylsulfonamidobenzofuran hydrochloride, 2-n-butyl-3-[4-(3-di-n-butylaminopropoxy)benzoyl]-5-methylsulfonamidobenzofuran fumarate and 2-n-butyl-3-[4-(3-di-n-butylaminopropoxy)benzoyl]-5-methylsulfonamidobenzofuran oxalate.

The antiarrhythmic compounds used in the context of the invention, notably dronedarone and amiodarone, in the form of base, or salts thereof, in particular the hydrochloride salts thereof, are characterized by low solubility in aqueous media, which constitutes a major drawback for making the active principle available by the oral route. Thus, these antiarrhythmic compounds have low solubility in simulated gastric medium (3 mg/ml at pH=1.5) and very low solubility in simulated intestinal medium (1 µg/ml at pH=6.5).

As an example, the solubility curve of dronedarone hydrochloride at room temperature and as a function of the pH shows maximum solubility of about 1 to 2 mg/ml around pH of 3 to 5, but very low solubility at pH of the order of 6 to 7, since it is no more than 10 µg/ml at pH=7. As for amiodarone hydrochloride, its solubility, at room temperature, is from 0.3 to 0.9 mg/ml in the pH range from 3 to 4 and a few µg/ml at pH=7. Thus, it is possible to dissolve 400 mg of dronedarone hydrochloride in 200 ml of aqueous medium buffered at pH=4 (0.1M $NaH_2PO_4$ aqueous solution). In contrast, in this medium diluted to 1/10 with an aqueous solution buffered at pH=7 (0.1M $Na_2HPO_4$ aqueous solution), dronedarone hydrochloride is precipitated (final pH of the medium=6.7). As these solubility conditions are similar to those recorded in the gastrointestinal tract, it can be assumed that, in the stomach, dronedarone hydrochloride will be subject to acidic conditions favorable to its dissolution, but once it enters the intestine, it will in contrast encounter a medium with pH between 6 and 7, i.e. a nonsolubilizing medium, in which it risks being precipitated.

Now, it is mainly in the intestine that absorption of the active principle takes place, and it is now well known that administration by the oral route requires optimal maintenance of the active principle in solution, in the hope of obtaining sufficient permeation along the gastrointestinal tract, and therefore acceptable exposure, for a significant therapeutic effect.

Taking into account the problem of solubility and bioavailability, a dosage form has been developed and is currently on the market, in the form of a film-coated tablet of 426 mg of dronedarone hydrochloride, equivalent to 400 mg of dronedarone, sold under the trade name Multaq®, for which the recommended dosage for adults is one tablet twice daily and this must be taken with a meal for ensuring optimal action of said active principle.

In fact, from the standpoint of pharmacokinetics, after oral administration with a meal, dronedarone is absorbed well (at least 70%). However, owing to presystemic first-pass metabolism, the absolute bioavailability of this medicinal product (taken with food) is no more than 15%. The concomitant consumption of food multiplies the bioavailability of the product by a factor of 2 to 4 relative to taking the medicine without simultaneous ingestion of food. After oral administration with a meal, the peak plasma concentrations of dronedarone and of its main circulating active metabolite (N-debutylated metabolite) are reached in 3 to 6 hours. The pharmacokinetics of dronedarone and of its N-debutylated metabolite deviate moderately from the rule of proportionality to dose: doubling the dose leads to an increase in Cmax and AUC by a factor of about 2.5 to 3.0.

Now, it is of course preferable for a patient to be able to have therapeutic treatment without the constraint of taking medicine with or without a meal, quite particularly in the area of the treatment of disorders of cardiac rhythm, especially arrhythmias.

The development of a pharmaceutical composition for oral administration of an active principle with antiarrhythmic activity, capable of producing acceptable bioavailability, regardless of whether or not food is ingested concomitantly, i.e. a composition involving a limited meal effect to be effective, is therefore still of considerable interest.

A new pharmaceutical composition has now been found, quite surprisingly and unexpectedly, allowing oral administration of at least one antiarrhythmia active principle, advantageously 2-n-butyl-3-[4-(3-di-n-butylaminopropoxy)benzoyl]-5-methylsulfonamidobenzofuran or a derivative of the latter, for example a salt thereof, without the drawbacks mentioned above. This composition, comprising at least one active principle incorporated in a matrix consisting of the other ingredients of said composition, in particular the other excipients, proves sufficiently stable and has suitable solubility for surviving in the gastrointestinal tract until it reaches the site of absorption. This composition can, moreover, be taken on an empty stomach or with a snack or even a low-fat meal and in one or more doses.

The present invention thus relates to a pharmaceutical composition for oral administration of an active principle with antiarrhythmic activity, such as for example 2-n-butyl-3-[4-(3-di-n-butylaminopropoxy)benzoyl]-5-methylsulfonamidobenzofuran (i) in the form of base, (ii) in the form of a pharmaceutically acceptable salt, characterized in that it comprises, besides said active principle, at least one amphiphilic lipid excipient with HLB value between 2 and 20.

The present invention thus relates to a pharmaceutical composition for oral administration of an active principle with antiarrhythmic activity, such as for example 2-n-butyl-3-[4-(3-di-n-butylaminopropoxy)benzoyl]-5-methylsulfonamidobenzofuran (i) in the form of base, (ii) in the form of a pharmaceutically acceptable salt, characterized in that it comprises, besides said active principle, at least one amphiphilic lipid excipient with HLB value between 1 and 20.

Said composition according to the invention can be in a dosage form of the capsule type or semi-solid or liquid capsule. In fact, it can advantageously be packaged in a dosage form of the capsule type, even more advantageously of the hard capsule type.

The following terms are used in the context of the present invention:

Capsule, a dosage form with a hard or soft shell;

Hard capsule, a capsule with a hard shell, having two parts: a part called the body and a part called the cap;

Bioavailability, a term used for describing a pharmacokinetic property of medicinal products, namely the fraction of a dose that reaches the bloodstream. It evaluates the amount of medicinal product absorbed that reaches the bloodstream and the rate of absorption of said medicinal product;

Active principle, any substance possessing a therapeutic effect, for example an antiarrhythmic effect. In the context of the invention, it is in particular any benzofuran derivative with antiarrhythmic activity, defined below, in particular dronedarone in the form of base, in the form of pharmaceutically acceptable salts of addition to organic or inorganic acids. Said salts can be prepared with pharmaceutically acceptable acids, but the salts of other acids that can be used, for example, for purification or isolation of the compounds of formula (I) also form part of the invention.

Excipient, any substance that is inactive or inert with respect to a living organism, in contrast to the active principle, and which facilitates the preparation and administration of a medicinal product;

Lipid excipient, any excipient known by a person skilled in the art as a lipid solvent, advantageously amphiphilic, having an HLB value (term defined below), which according to the invention is below 20 and above 1;

Matrix, all the ingredients other than the active principle or principles of the composition according to the invention, in particular the excipients;

HLB value, the value of the hydrophilic-lipophilic balance, according to the classification developed by Griffin, which is well known by a person skilled in the art;

Surfactant, an excipient, which through its amphiphilic properties facilitates the wetting of powders, improves solubility/dissolution and/or slows reprecipitation;

Co-solvent, any solvent improving the feasibility of the method of manufacture of the composition according to the invention on the basis of the key parameters of viscosity and melting point of the matrix of said composition as well as dissolution or dispersion of the active principle in said matrix;

Diluent, an excipient used for obtaining a sufficient volume of composition for manufacturing a dosage form, for example a hard capsule, of the desired size and possessing suitable physical characteristics for the method of manufacture selected for the hard capsule;

Disintegrant, an excipient that provides satisfactory disintegration of the dosage form and therefore disintegration of the active principle in the stomach by increasing the friability and by reducing the hardness of the dosage form;

Antiadherent, an excipient intended to prevent the particles sticking to one another and to the manufacturing equipment during manufacture of the dosage form, for example when filling the capsules.

Lubricant, an excipient intended to facilitate the steps in manufacture of the dosage form, owing to their role in sliding, i.e. consisting of increasing the flowability of the particles in the pipework of the machines;

Plasticizer, an excipient intended to permit constant release of the active principle from the dosage form by being interposed between the polymer chains and by allowing them to slide relative to one other. It is selected in relation to its solubility.

Among the compositions according to the invention, we may mention a first group of pharmaceutical compositions comprising:

1-60 wt % of at least one active principle according to the invention, advantageously between 1 and 50%, even more advantageously between 10 and 45%, even better between 20% and 40%;

40-99 wt % of at least one lipid excipient according to the invention, advantageously between 45 and 80%, even more advantageously between 50% and 60%, 0-30 wt % of at least one compound selected from surfactants, co-solvents, diluents, disintegrants, lubricants, organic or inorganic bases and plasticizers, advantageously from 1 to 20%, even better from 1 to 10%, the percentages being expressed by weight relative to the total weight of said composition.

Among the compositions according to the invention, we may mention a second group of pharmaceutical compositions comprising:

1-60 wt % of at least one active principle according to the invention, advantageously between 1 and 50%, even more advantageously between 10 and 45%, even better between 20% and 40%;

37-99 wt % of at least one lipid excipient according to the invention, advantageously between 45 and 80%, even more advantageously between 45% and 55%, 0-30 wt % of at least one compound selected from surfactants, co-solvents, diluents, disintegrants, lubricants, organic or inorganic bases and plasticizers, advantageously from 1 to 20%, even better from 1 to 10%, the percentages being expressed by weight relative to the total weight of said composition.

Among the compositions according to the invention, we may mention a third group of pharmaceutical compositions comprising:
- 1-60 wt % of at least one active principle according to the invention, advantageously between 1 and 50%, even more advantageously between 10 and 45%, even better between 20% and 40%;
- 40-99 wt % of at least one lipid excipient according to the invention, advantageously between 45 and 80%, even more advantageously between 50% and 60%,
- 0-30 wt % of at least one surfactant, advantageously between 1% and 20%, even more advantageously between 5% and 15%, and
- 0-29 wt % of at least one co-solvent, advantageously between 1 and 20%, even more advantageously between 2 and 15%;

the percentages being expressed by weight relative to the total weight of said composition. The total of the compositions comes to 100 wt %.

Among the compositions according to the invention, we may mention a fourth group of pharmaceutical compositions comprising:
- 1-60 wt % of at least one active principle according to the invention, advantageously between 1 and 50%, even more advantageously between 10 and 45%, even better between 20% and 40%;
- 37-99 wt % of at least one lipid excipient according to the invention, advantageously between 45 and 80%, even more advantageously between 50% and 60%,
- 0-30 wt % of at least one surfactant, advantageously between 1% and 20%, even more advantageously between 5% and 10%, and
- 0-29 wt % of at least one co-solvent, advantageously between 1 and 20%, even more advantageously between 2 and 15%;

the percentages being expressed by weight relative to the total weight of said composition. The total of the compositions comes to 100 wt %.

Among the compositions according to the invention, we may mention a fifth group of pharmaceutical compositions comprising:
- 60-200 wt % of at least one lipid excipient according to the invention, advantageously between 120 and 180%, even more advantageously 180%
- 0-30 wt % of at least one surfactant, advantageously between 5% and 30%, even more advantageously between 10% and 30%,
- 0-30 wt % of at least one co-solvent, advantageously between 1 and 20%;

the percentages being expressed by weight relative to the total weight of the active principle.

The pharmaceutical compositions according to the invention comprise at least one active principle with antiarrhythmic activity and at least one lipid excipient.

Among the active principles with antiarrhythmic activity according to the invention, we may mention 2-n-butyl-3-[4-(3-di-n-butylaminopropoxy)benzoyl]-5-methylsulfonamidobenzofuran in the form of base or dronedarone and the pharmaceutically acceptable salts thereof described in patent EP1315709.

As pharmaceutically acceptable salts, we may mention for example 2-n-butyl-3-[4-(3-di-n-butylaminopropoxy)benzoyl]-5-methylsulfonamidobenzofuran hydrochloride, 2-n-butyl-3-[4-(3-di-n-butylaminopropoxy)benzoyl]-5-methylsulfonamidobenzofuran fumarate and 2-n-butyl-3-[4-(3-di-n-butylaminopropoxy)benzoyl]-5-methylsulfonamidobenzofuran oxalate.

Advantageously, the composition according to the invention comprises 2-n-butyl-3-[4-(3-di-n-butylaminopropoxy)benzoyl]-5-methylsulfonamidobenzofuran or 2-n-butyl-3-[4-(3-di-n-butylaminopropoxy)benzoyl]-5-methylsulfonamidobenzofuran hydrochloride as active principle.

According to one variant, dissolution of the active principle in its base form can be obtained starting from pharmaceutically acceptable salts of dronedarone, as mentioned above, and by reforming the active principle in its base form in situ by change of pH with an organic or inorganic base.

The compositions according to the invention comprising at least one pharmaceutically acceptable salt of dronedarone, and further comprising at least one organic or inorganic base, advantageously in stoichiometric molar amount relative to the active principle in the form of base, form part of the present invention.

As a guide, the nature of the base that can be used in the composition can be organic, for example ethanolamine, or mineral such as for example soda or potash. Advantageously, it is soda.

The active principle or principles according to the invention is or are present in the composition according to the invention in a proportion in the range 1-60 wt %, advantageously between 1 and 50%, even more advantageously between 10 and 45%, even better between 20% and 40 wt % relative to the total weight of the composition.

The lipid excipient is an amphiphilic lipid excipient with HLB value between 1 and 20 and whose melting point is below 50° C.

The lipid excipient is an amphiphilic lipid excipient with HLB value between 2 and 20 and whose melting point is below 50° C.

A distinction is made between amphiphilic excipients that are semi-solid at room temperature and amphiphilic excipients that are liquid at room temperature.

The lipid excipient according to the invention can be selected from:
- semi-solid substituted glycerides,
- liquid substituted glycerides,
- semi-solid substituted polyoxylglycerides,
- liquid substituted polyoxylglycerides,
- and mixtures thereof.

We may mention, for example, a group in which the lipid excipient is selected from:
- as semi-solid substituted glycerides according to the invention, the Gelucires marketed for example under the brand name Gelucire® 33/01, Gelucire® 39/01, Gelucire® 43/01 and Geleol®, Peceol™,
- as liquid substituted glycerides according to the invention, those marketed for example under the name Labrafac Lipophile® WL1349,
- as semi-solid substituted polyoxylglycerides according to the invention, the Gelucire marketed for example under the brand name Gelucire® 44/14, Gelucire® 50/13,
- as liquid substituted polyoxylglycerides according to the invention, those marketed for example under the brand name Labrafil® M1944CS, Labrafil® M2125CS, Labrafil® M2130CS and Labrasol®.

We may mention, for example, another group in which the lipid excipient is selected from semi-solid substituted polyoxylglycerides according to the invention, the commercially available Gelucire, more particularly the lauroyl macroglyceride marketed under the brand name Gelucire® 44/14.

When the active principle is in the form of a salt, the composition can be in the form of a dispersion of said solid active principle in a solid matrix at room temperature in the case when a semi-solid lipid excipient is used in a sufficient amount or in the form of a dispersion of a solid in an oil at room temperature in the case when a liquid lipid excipient is used in a sufficient amount, the solubility of said active principle in the composition being moreover a function of the pH of the medium in which the composition is contained.

The amphiphilic lipid excipient, semi-solid at room temperature, of the composition according to the invention, has the advantage of permitting a solid dispersion or hot dissolution of the active principle in the matrix of said composition and of facilitating dissolving of the active principle on dissolution of the matrix in the gastric and/or intestinal aqueous environment.

The amphiphilic lipid excipient, liquid at room temperature, of the composition according to the invention, has the advantage of facilitating dissolving of the active principle in the gastric and/or intestinal aqueous environment.

Advantageously, the composition according to the invention comprises at least one amphiphilic lipid excipient, having an HLB value between 5 and 18.

The amphiphilic lipid excipients, with HLB value between 5 and 18, according to the invention, can be selected from the group comprising:
   the medium-chain mono- and diglycerides, for example Capmul MCM® (HLB value between 5.5 and 6), marketed by the company Abitec,
   propylene glycol monolaurate, for example Lauroglycol® 90 (HLB value equal to 5) and Capmul PG12®, marketed by the companies Gattefosse and Abitec respectively,
   the caprylocaproyl macrogol-8 glycerides, for example Labrasol® (HLB value equal to 14), marketed by the company Gattefosse,
   the lauroyl macrogolglycerides, for example Gelucire® 44/14 (HLB value equal to 14) and Gelucire® 50/13 (HLB value equal to 13), marketed by the company Gattefosse,
   propylene glycol caprylic acid monoester, for example Capmul® PG-8 (HLB value equal to 6), marketed by the company Abitec,
   and mixtures thereof.

More particularly, the amphiphilic lipid excipient with HLB value between 5 and 18 is selected from the group comprising Capmul MCM®, Lauroglycol® 90, Capmul PG12®, Labrasol®, Gelucire® 44/14, Gelucire® 50/13, Capmul® PG-8, and mixtures thereof.

According to one embodiment, the lipid excipients according to the invention are selected from the amphiphilic lipid excipients, having an HLB value between 12 and 18.

The lipid excipient or excipients according to the invention is or are present in the composition according to the invention in a proportion in the range 40-99 wt %, advantageously between 45 and 80%, even more advantageously between 50% and 60 wt % relative to the total weight of the composition.

The lipid excipient or excipients according to the invention is or are present in the composition according to the invention in a proportion in the range 37-99 wt %, advantageously between 45 and 80%, even more advantageously between 50% and 60 wt % relative to the total weight of the composition.

The lipid excipient or excipients according to the invention is or are present in the composition according to the invention in a proportion in the range 100-200 wt %, advantageously between 110 and 180%, even more advantageously between 50% and 60 wt % relative to the total weight of the active principle.

The pharmaceutical compositions according to the invention can further comprise at least one surfactant and/or at least one co-solvent.

The surfactant is advantageously hydrophilic and/or non-ionic. It can be selected from:
   ethylene oxide/propylene oxide copolymers, called poloxamers hereinafter, such as poloxamer 124 marketed under the brand name SYNPERONIC PE/L44; poloxamer 188 marketed under the brand name PLURONIC F68 or SYNPERONIC PE/F68; poloxamer 237 marketed under the brand name PLURONIC F87 or SYNPERONIC PE/F87; poloxamer 338 marketed under the brand name SYNPERONIC PE/F108 or poloxamer 407 marketed under the brand name PLURONIC F127, SYNPERONIC PE/F127 or LUTROL F127;
   polyethoxylated castor oils, such as those marketed under the brand name CREMOPHOR RH40;
   ethoxylated polysorbates, such as polysorbate 20, polysorbate 40, polysorbate 60 and polysorbate 80 marketed respectively under the brand names TWEEN 20, TWEEN 40, TWEEN 60, and TWEEN 80; and
   polyethylene hydroxystearates, such as polyethylene hydroxystearate 660 marketed under the brand name SOLUTOL HS15.

More particularly, the surfactant can be selected from:
   ethylene oxide/propylene oxide copolymers, called poloxamers hereinafter, such as poloxamer 124 marketed under the brand name SYNPERONIC PE/L44; poloxamer 188 marketed under the brand name PLURONIC F68 or SYNPERONIC PE/F68; or poloxamer 407 marketed under the brand name PLURONIC F127, SYNPERONIC PE/F127 or LUTROL F127;
   polyethoxylated castor oils, such as those marketed under the brand name CREMOPHOR RH40;
   ethoxylated polysorbates, such as polysorbate 60 marketed under the brand name TWEEN 60; and
   polyethylene hydroxystearates, such as polyethylene hydroxystearate 660 marketed under the brand name SOLUTOL HS15.

Advantageously, the surfactant or surfactants according to the invention is or are selected from the ethylene oxide/propylene oxide copolymers called poloxamers, even more advantageously it is poloxamer 407.

Said surfactant can be present in the composition according to the invention at a rate from 0% to 30 wt % relative to the total weight of said composition, advantageously between 1% and 20 wt %, even more advantageously from 5% to 15 wt % of surfactant.

Said surfactant can be present in the composition according to the invention at a rate of 0-30 wt % of at least one surfactant, advantageously between 5% and 20%, even more advantageously between 10% and 20%, by weight relative to the total weight of active principle.

The co-solvent according to the invention can be selected from the alcoholic organic solvents or the glycol derivatives.

We may mention as co-solvent:
   alcohols such as ethanol and isopropanol for example;
   propylene glycol and derivatives thereof, optionally substituted, such as those marketed under the brand name Labrafac® PG, Lauroglycol™ 90, Lauroglycol™ FCC, Capryol™ 90, Capryol™ PGMC.

Said co-solvent can be present in the pharmaceutical composition according to the invention at a rate from 0% to 29 wt % relative to the total weight of said composition, advantageously between 1% and 20 wt %, even more advantageously from 2% to 15 wt % of co-solvent.

Said co-solvent can be present in the pharmaceutical composition according to the invention at a rate of 0-30 wt % of at least one co-solvent, advantageously between 1 and 20%, by weight relative to the total weight of active principle.

According to one embodiment, the co-solvent is a glycol derivative, substituted and/or at a content below 29 wt % relative to the total weight of said composition, advantageously the co-solvent is propylene glycol and/or at a content of about 20 wt %.

According to one embodiment, the co-solvent is a glycol derivative, substituted and/or at a content below 30 wt % relative to the total weight of active principle, advantageously the co-solvent is propylene glycol and/or at a content of about 20 wt % relative to the total weight of the active principle.

According to one embodiment, the composition according to the invention comprises:
- 2-n-butyl-3-[4-(3-di-n-butylaminopropoxy)benzoyl]-5-methylsulfonamidobenzofuran or 2-n-butyl-3-[4-(3-di-n-butylaminopropoxy)benzoyl]-5-methylsulfonamidobenzofuran hydrochloride in the form of base, as active principle, and/or
- at least one semi-solid lipid excipient with HLB between 1 and 20, advantageously between 5 and 18, even more advantageously between 12 and 18, advantageously selected from the semi-solid substituted glycerides and the semi-solid substituted polyoxylglycerides, advantageously it is Gelucire® 44/14, and/or
- at least one surfactant, advantageously selected from the ethylene oxide/propylene oxide copolymers called poloxamers, even more advantageously it is poloxamer 407, and optionally at least one co-solvent as defined above.

This pharmaceutical composition is in a liquid or semi-solid form, i.e. of a pasty consistency, depending on the consistency and nature of the excipient or excipients used, among others of the lipid excipient, at room temperature. A lipid or semi-solid excipient at room temperature will give rise to the formation of a semi-solid matrix and therefore to a composition according to the invention of a pasty consistency whereas a lipid excipient that is liquid at room temperature will give rise to the formation of a liquid matrix and therefore to a composition according to the invention of a liquid consistency.

Thus, in the case when the lipid excipient according to the invention is selected from the lipid or semi-solid excipients, the composition according to the invention can be prepared by employing known methods for solubilization or cold or hot solid dispersion in the lipid excipient forming a lipid matrix. The manufacture of the composition consists, for example, of dissolving or dispersing the active principle according to the invention and optionally other excipients according to the invention, in said lipid excipient at a temperature from about 30° C. to 60° C., for example a temperature of about 44° C., said temperature being selected as a function of the melting point of said lipid excipient used.

According to a particularly advantageous embodiment, the method of manufacturing the composition according to the invention consists of dissolving the active principle, advantageously 2-n-butyl-3-[4-(3-di-n-butylaminopropoxy)benzoyl]-5-methylsulfonamidobenzofuran in the form of base, at about 44° C. in the lipid excipient, advantageously lauryl macroglycerides, for example Gelucire® 44/14.

In the case when the lipid excipient, according to the invention, is selected from the liquid lipid excipients, the composition according to the invention can be prepared by employing known methods of dissolving or dispersing the active principle in the lipid excipient, forming a lipid matrix that is liquid at room temperature.

The methods of preparing the pharmaceutical compositions according to the invention are carried out by the conventional techniques known by a person skilled in the art.

The liquid or semi-solid pharmaceutical composition according to the invention, thus obtained, can then be incorporated in a hard capsule, as it is. Encapsulation is carried out according to the conventional methods of encapsulation, taking into account the physicochemical constraints of said composition and of said method.

Said composition can optionally be transformed into powders, which can be granulated or optionally can be incorporated in capsules or used as they are.

The invention thus also relates to a dosage form comprising a pharmaceutical composition according to the invention.

This dosage form can be in the form of a capsule containing the composition according to the invention or optionally in the form of powders or granules that can be supplied in multidose containers or in the form of unit doses such as packets or sachets.

Capsules are solid preparations consisting of a hard or soft shell, of variable shape and capacity, generally containing a unit dose of active principle. The shell is based on gelatin or other natural or synthetic substances whose consistency can be adjusted by adding for example glycerol or sorbitol. Other excipients such as surfactants, opacifiers, antimicrobial preservatives, sweeteners, colorants and/or flavorings can also be added to the composition of the capsule shells.

We may mention as capsules: hard capsules, soft shell capsules, enteric capsules and modified-release capsules.

Advantageously, the dosage form according to the invention is a hard capsule.

The method of manufacture of hard capsules comprising a body and a cap consists of (i) preparing the composition according to the invention by mixing the ingredients as defined above and then (ii) filling the cap and/or body parts of the capsule by volumetric distribution by a method that is suitable for powders (compressing/metering apparatus, a leveling method, a method with alternating leveling and packing or tamping, an endless-screw method or a method of cell metering) or for semi-solids (casting of the molten or liquid product), and finally closing the capsules by joining together the parts forming the cap and body of said capsule.

In the case of soft capsules the liquid preparation is poured at the same time as the capsule is formed in the dies according to the conventional method of manufacture.

As a nonlimiting guide, the amount of active principle can vary from 50 to 500 mg per dosage unit such as for example (i) a capsule, advantageously a hard capsule, or (ii) a sachet of powders, or granules, and the amount of lipid excipient between 0.5 and 100 mg. Preferably, a dosage form according to the invention, for example a hard capsule, can comprise from 200 to 400 mg of active principle.

The pharmaceutical composition according to the invention and the dosage form comprising said composition aim to limit the meal effect after oral administration in humans. The lipid excipient makes it possible on the one hand to solubilize the active principle according to the invention and on the other hand to protect it from the negative effects of the pH in the intestinal tract, thus permitting significant avoidance of the meal effect. The presence of a surfactant, for example poloxamer, in said composition makes it possible to limit the reprecipitation and agglomeration of the active principle while in the gastrointestinal tract.

Figure 1:
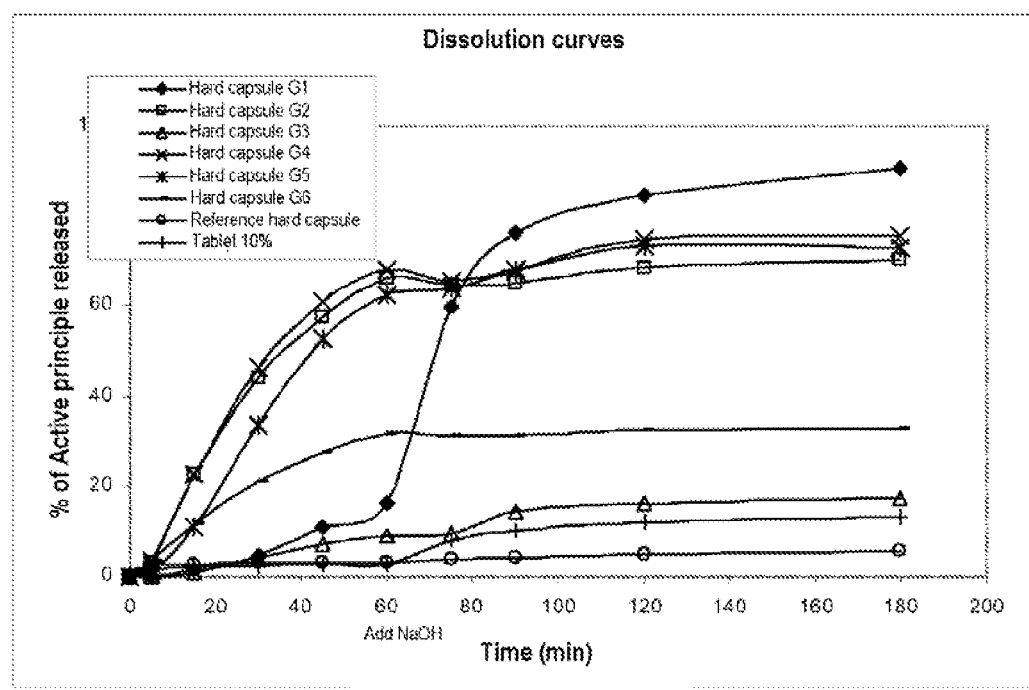
FIG. 1 shows the dissolution curves of hard capsules according to the invention (Hard Capsules G1 to Hard Capsules G6), of a comparative reference hard capsule and of a comparative tablet with 10% of poloxamer, all these formulations containing active principle according to the invention.

These curves express the percentage by weight of active principle released as a function of time, expressed in minutes. The vertical line shown in bold at 60 min marks the moment when an alkaline solution of NaOH is added to the simulated gastric medium in order to simulate an intestinal medium.

EXAMPLES

Table A below shows the solubility of dronedarone hydrochloride and of dronedarone base form in lipid excipients according to the invention.

TABLE A

| | | Solubility (mg/ml) | | |
|---|---|---|---|---|
| Excipients | HLB | Dronedarone Hydrochloride | Dronedarone Base | Temp. |
| Oleic acid | — | — | >341.4 | RT |
| Capmul PG8 | 5 | 10.04 | 517.1 | RT |
| Captex 355 | — | 0.0353 | 166.7 | RT |
| Cremophor RH 40 | 14 | 14.77 | >312.7 | 55° C. |

TABLE A-continued

| | | Solubility (mg/ml) | | |
|---|---|---|---|---|
| Excipients | HLB | Dronedarone Hydrochloride | Dronedarone Base | Temp. |
| Crodamol EO (ethyl oleate) | — | — | 153.5 | RT |
| ethanol | NA | — | >500* | RT |
| Gelucire 44/14 | 14 | — | 632.6 | 55° C. |
| Gelucire 43/01 | 1 | 0.0445 | 259.0 | 55° C. |
| Gelucire 33/01 | 1 | 0.0962 | 371.3 | 55° C. |
| sweet almond oil | 1 | — | 45.2 | RT |
| soybean oil | 1 | 0.0231 | 60.7*/87.7 | RT |
| Lipophilic Labrafac | 1 | 0.0251 | 128.7 | RT |
| Labrafac PG | 2 | 0.0416 | 183.6 | RT |
| Labrafil M1944Cs | 4 | 0.5041 | 208.5*/192.6 | RT |
| Labrasol | 14 | — | >400* | RT |
| Labrasol ALF | 14 | 4.84 | 401.3 | RT |
| Lauroglycol 90 | 4 | 2.09 | 310.6 | RT |
| Miglyol 812N | 1 | 0.0409 | 143.5*/141.6 | RT |
| PEG 400 | NA | 13.2* | 273.1*/280.1 | RT |
| propylene glycol | NA | 15.8* | 18.2* | RT |

Co-solvents

Compositions according to the invention were manufactured, with the composition shown in detail in Tables 1, 3 and 4 below.

Comparative compositions, not according to the invention, were manufactured with the composition detailed in Table 2 below. The amounts of compounds used for making said compositions are expressed in mg in said Tables 1 and 2.

"-" signifies absence of the composition.
"QS" signifies in sufficient quantity.
"HCl Salt" signifies dronedarone hydrochloride.
"Base" signifies dronedarone base form.
"Pol." signifies "poloxamer".
"Geluc." signifies "Gelucire".
"Crem. RH40" signifies "Cremophor RH40"

TABLE 1

| Ingredients | EX 1 (mg) | EX 2 (mg) | EX 3 (mg) | EX 4 (mg) | EX 5 (mg) | EX 6 (mg) |
|---|---|---|---|---|---|---|
| Dronedarone in the form of hydrochloride | 213.0 | 213.0 | 213.0 | — | — | — |
| Dronedarone in the form of base | — | — | — | 200.0 | 200.0 | 200.0 |
| Lauroyl macrogolglycerides (Gelucire 44/14) | 357.0 | 343.7 | 237.0 | 343.7 | 357.0 | 237.0 |
| Poloxamer 407 | 60.0 | 60.0 | — | 60.0 | 60.0 | — |
| Sodium hydroxide* | — | 14.4 | — | — | — | — |
| Distilled water* | — | 38.9 | — | 38.9 | — | — |
| Propylene glycol | 40.0 | — | — | — | 40.0 | — |
| Total weight (mg) | 670.0 | 670.0 | 450.0 | 642.6 | 657.0 | 437.0 |
| Dosage form Hard capsule | G1 | G2 | G3 | G4 | G5 | G6 |

*corresponds to an aqueous solution at 27% sodium hydroxide

The composition diluted to one part per hundred of these formulations G1 to G6 and of other formulations according to the invention is expressed in Tables 3 and 4 below.

TABLE 3

| | Composition diluted to one part per hundred relative to the total formula | | | |
|---|---|---|---|---|
| Hard capsule | % active principle (eq base) | % of Gelucire | % of surfactant (SA) | % of propylene glycol (co-solvent) |
| G1 | 30 (HCl salt) | 53 (Geluc. 44/14) | 9 (Pol. 407) | 6 |
| G2 | 30 (HCl salt) | 51 (Geluc. 44/14) | 9 (Pol. 407) | 0 |

TABLE 3-continued

Composition diluted to one part per hundred relative to the total formula

| Hard capsule | % active principle (eq base) | % of Gelucire | % of surfactant (SA) | % of propylene glycol (co-solvent) |
|---|---|---|---|---|
| G3 | 44 (HCl salt) | 53 (Geluc. 44/14) | 0 | 0 |
| G4 | 31 (Base) | 53 (Geluc. 44/14) | 9 (Pol. 407) | 0 |
| G5 | 30 (Base) | 54 (Geluc. 44/14) | 9 (Pol. 407) | 6 |
| G6 | 46 (Base) | 54 (Geluc. 44/14) | 0 | 0 |
| G7 | 63 (400 mg base) | 37 (Geluc. 44/14) | 0 | 0 |
| G8 | 36 (200 mg base) | 64 (Geluc. 44/14) | 0 | 0 |
| G9 (=G1 without SA) | 33 (HCl salt) | 59 (Geluc. 44/14) | 0 | 7 |
| G10 (=G5 without SA) | 34 (Base) | 60 (Geluc. 44/14) | 0 | 7 |
| G11 (=G1 with 5% SA) | 32 (HCl salt) | 58 (Geluc. 44/14) | 2 (Pol. 407) | 6 |
| G12 (=G1 with 10% SA) | 32 (HCl salt) | 57 (Geluc. 44/14) | 3 (Pol. 407) | 6 |
| G13 (=G5 with 10% SA) | 32 (Base) | 58 (Geluc. 44/14) | 3 (Pol. 407) | 6 |
| G14 | 30 (HCl salt) | 53 (Geluc. 33/01) | 9 | 6 |
| G15 | 30 (base) | 54 (Geluc. 33/01) | 9 | 6 |
| G16 | 33 (HCl salt) | 59 (Geluc. 33/01) | 0 | 7 |
| G17 | 34 (base) | 60 (Geluc. 33/01) | 0 | 7 |
| G18 | 30 (HCl salt) | 53 (Geluc. 43/01) | 9 | 6 |
| G19 | 30 (base) | 54 (Geluc. 43/01) | 9 | 6 |
| G20 | 33 (HCl salt) | 59 (Geluc. 43/01) | 0 | 7 |
| G21 | 34 (base) | 60 (Geluc. 43/01) | 0 | 7 |
| G22 | 30 (HCl salt) | 53 (Geluc. 44/14) | 9 (Pol. 188) | 6 |
| G23 | 30 (base) | 54 (Geluc. 44/14) | 9 (Pol. 188) | 6 |
| G24 | 30 (HCl salt) | 53 (Geluc. 44/14) | 9 (Crem. RH40) | 6 |
| G25 | 30 (base) | 54 (Geluc. 44/14) | 9 (Crem. RH40) | 6 |
| G26 | 30 (HCl salt) | 53 (Geluc. 44/14) | 9 (Pluronic L44) | 6 |
| G27 | 30 (base) | 54 (Geluc. 44/14) | 9 (Pluronic L44) | 6 |
| G28 | 30 (HCl salt) | 54 (Geluc. 44/14) | 9 (Tween 60) | 6 |
| G29 | 30 (base) | 54 (Geluc. 44/14) | 9 (Tween 60) | 6 |

TABLE 4

Composition diluted to one part per hundred relative to the active principle

| Hard capsule | % of Gelucire | % of surfactant | % of propylene glycol (co-solvent) |
|---|---|---|---|
| G1 | 179 (Geluc. 44/14) | 30 (Pol. 407) | 20 |
| G2 | 172 (Geluc. 44/14) | 30 (Pol. 407) | 0 |
| G3 | 119 (Geluc. 44/14) | 0 | 0 |
| G4 | 172 (Geluc. 44/14) | 30 (Pol. 407) | 0 |
| G5 | 179 (Geluc. 44/14) | 30 (Pol. 407) | 20 |
| G6 | 119 (Geluc. 44/14) | 0 | 0 |
| G7 | 59 (Geluc. 44/14) | 0 | 0 |
| G8 | 179 (Geluc. 44/14) | 0 | 0 |

TABLE 4-continued

Composition diluted to one part per hundred relative to the active principle

| Hard capsule | % of Gelucire | % of surfactant | % of propylene glycol (co-solvent) |
|---|---|---|---|
| G9 (=G1 without SA) | 179 (Geluc. 44/14) | 0 | 20 |
| G10 (=G5 without SA) | 179 (Geluc. 44/14) | 0 | 20 |
| G11 (=G1 with 5% SA) | 179 (Geluc. 44/14) | 5 (Pol. 407) | 20 |
| G12 (=G1 with 10% SA) | 179 (Geluc. 44/14) | 10 (Pol. 407) | 20 |
| G13 (=G5 with 10% SA) | 179 (Geluc. 44/14) | 10 (Pol. 407) | 20 |
| G14 | 179 (Geluc. 33/01) | 30 (Pol. 407) | 20 |
| G15 | 179 (Geluc. 33/01) | 30 (Pol. 407) | 20 |
| G16 | 179 (Geluc. 33/01) | 0 | 20 |
| G17 | 179 (Geluc. 33/01) | 0 | 20 |
| G18 | 179 (Geluc. 43/01) | 30 (Pol. 407) | 20 |
| G19 | 179 (Geluc. 43/01) | 30 (Pol. 407) | 20 |
| G20 | 179 (Geluc. 43/01) | 0 | 20 |
| G21 | 179 (Geluc. 43/01) | 0 | 20 |
| G22 | 179 (Geluc. 44/14) | 30 (Pol. 188) | 20 |
| G23 | 179 (Geluc. 44/14) | 30 (Pol. 188) | 20 |
| G24 | 179 (Geluc. 44/14) | 30 (Cremophor RH40) | 20 |
| G25 | 179 (Geluc. 44/14) | 30 (Cremophor RH40) | 20 |
| G26 | 179 (Geluc. 44/14) | 30 (Pluronic L44) | 20 |
| G27 | 179 (Geluc. 44/14) | 30 (Pluronic L44) | 20 |
| G28 | 179 (Geluc. 44/14) | 30 (Tween 60) | 20 |
| G29 | 179 (Geluc. 44/14) | 30 (Tween 60) | 20 |

Opaque white capsules of size 0 were then manufactured using the compositions from the examples given below and using comparative composition 2 for obtaining hard capsules G1-G29 according to the invention and a hard capsule not according to the invention, i.e. reference hard capsule. Comparative composition 1, not according to the invention, was used for making a tablet that is not according to the invention.

TABLE 2

| Ingredients | Comparative Composition 1 (mg) | Comparative Composition 2 (mg) |
|---|---|---|
| Dronedarone in the form of hydrochloride | 426 | 213 |
| pregelatinized starch | 60.0 | 86.2 |
| lactose EFC | QS | 129.2 |
| talc | — | 48.0 |
| colloidal silica | 2.4 | 1.2 |
| magnesium stearate | 6.0 | 2.4 |
| Hypromellose 6 mPa·s | 12.0 | — |
| crospovidone | 30.0 | — |
| Poloxamer40 | 40 | — |
| Total weight (mg) | 640 | 480 |
| Dosage form | Tablet 10% | Reference hard capsule |

The equipment required for making the compositions and the hard capsules, for which the procedures are described below, is as follows: Magnetic stirrer, Beaker, Precision balance adjusted to the amount weighed, Sieve 0.315 mm, Water bath, Gilson Pipette 1000 μL piston-type, Capsuling machine.

Moreover, the Gelucire 44/14 used for making the compositions is stoved at 55° C. in the evening of the day before manufacture. Homogenization is done manually by inverting the pot.

Manufacture of Hard Capsule G1:
Procedure:
Weigh the Gelucire® 44/14 previously melted in the beaker used for manufacture,
Sieve the dronedarone in the form of hydrochloride at 0.315 mm mesh before weighing,
Melt and mix the Gelucire® 44/14 and poloxamer 407, stirring slowly at a stirrer speed of 200 rpm for about 10 min at a water bath temperature of 55-60° C.,
Add the propylene glycol at a stirrer speed of 200 rpm and at a water bath temperature of 55-60° C.,
Slowly add, and disperse with vigorous stirring, the previously sieved dronedarone hydrochloride at a speed during addition of 300-650 rpm. After addition, mix for 30 min at a mixing speed of 500 rpm and at a water bath temperature of 55-60° C.,
With an automatic pipette, fill opaque white hard capsules size 0. Fill the capsules with unit weights. The stirring speed during distribution is 500 rpm and the water bath temperature is 55-60° C.,
After closure, arrange the capsules in the vertical position on the capsuling machine for solidification at room temperature.

Manufacture of Hard Capsule G2:
Procedure:
Weigh the Gelucire® 44/14 previously melted in the beaker used for manufacture,
Sieve the dronedarone in the form of hydrochloride at 0.315 mm mesh before weighing,
Melt and mix the Gelucire® 44/14 and poloxamer 407, stirring slowly at a stirrer speed of 200 rpm for about 10 min at a water bath temperature of 55-60° C.,
Slowly add, and disperse with vigorous stirring, the previously sieved dronedarone hydrochloride at a speed during addition of 300-650 rpm.
After addition, mix for 10 min at a mixing speed of 500 rpm at a water bath temperature of 55-60° C.,
Add 27% sodium hydroxide solution at a stirring speed of 500 rpm. After addition, mix for 30 min at a water bath temperature of 55-60° C.,
With an automatic pipette, fill opaque white hard capsules size 0. Fill the capsules with unit weights. The stirring speed during distribution is 500 rpm and the water bath temperature is 55-60° C., After closure, arrange the capsules in the vertical position on the capsuling machine for solidification at room temperature.

Manufacture of Hard Capsule G3:
Procedure:
Weigh the Gelucire® 44/14 previously melted in the beaker used for manufacture,
Sieve the dronedarone in the form of hydrochloride at 0.315 mm mesh before weighing,
Slowly add, and disperse with vigorous stirring, the previously sieved dronedarone hydrochloride at a speed during addition of 300-650 rpm. After addition, mix for 30 min at a mixing speed of 350 rpm and at a water bath temperature of 55-60° C.,
With an automatic pipette, fill opaque white hard capsules size 0. Fill the capsules with unit weights. The stirring speed during distribution is 500 rpm and the water bath temperature is 55-60° C.,
After closure, arrange the capsules in the vertical position on the capsuling machine for solidification at room temperature.

Manufacture of Hard Capsule G4:
Procedure:
Weigh the Gelucire® 44/14 previously melted in the beaker used for manufacture,
Sieve the dronedarone at 0.315 mm mesh before weighing,
Melt and mix the Gelucire® 44/14 and poloxamer 407, stirring slowly at a stirrer speed of 200 rpm for about 10 min at a water bath temperature of 55-60° C.,
Gradually add and dissolve the previously sieved dronedarone in its base form, stirring vigorously at a speed during addition of 300-650 rpm. After addition, mix for 30 min at a mixing speed of 500 rpm and at a water bath temperature of 55-60° C.,
Gradually add the water, stirring at a stirrer speed of 500 rpm for about 10 min and at a water bath temperature of 55-60° C.,
With an automatic pipette, fill opaque white hard capsules size 0. Fill the capsules with unit weights. The stirring speed during distribution is 500 rpm and the water bath temperature is 55-60° C.,
After closure, arrange the capsules in the vertical position on the capsuling machine for solidification at room temperature.

Manufacture of Hard Capsule G5:
Procedure:
Weigh the Gelucire® 44/14 previously melted in the beaker used for manufacture,
Sieve the dronedarone at 0.315 mm mesh before weighing,
Melt and mix the Gelucire® 44/14 and poloxamer 407, stirring slowly at a stirrer speed of 200 rpm for about 10 min at a water bath temperature of 55-60° C.,
Add the propylene glycol at a stirrer speed of 200 rpm and at a water bath temperature of 55-60° C.,
Gradually add and dissolve the previously sieved dronedarone in its base form, stirring vigorously at a speed during addition of 300-650 rpm. After addition, mix for 30 min at a mixing speed of 500 rpm and at a water bath temperature of 55-60° C.,
With an automatic pipette, fill opaque white hard capsules size 0. Fill the capsules with unit weights. The stirring speed during distribution is 500 rpm and the water bath temperature is 55-60° C.,
After closure, arrange the capsules in the vertical position on the capsuling machine for solidification at room temperature.

Manufacture of Hard Capsule G6:
Procedure:
Weigh the Gelucire® 44/14 previously melted in the beaker used for manufacture,
Sieve the dronedarone at 0.315 mm mesh before weighing,
Melt and mix the Gelucire® 44/14, stirring slowly at a stirrer speed of 200 rpm for about 10 min at a water bath temperature of 55-60° C.,
Gradually add and dissolve the previously sieved dronedarone in its base form, stirring vigorously at a speed during addition of 300-650 rpm. After addition, mix for 30 min at a mixing speed of 500 rpm and at a water bath temperature of 55-60° C.,
With an automatic pipette, fill opaque white hard capsules size 0. Fill the capsules with unit weights. The stirring speed during distribution is 500 rpm and the water bath temperature is 55-60° C.,
After closure, arrange the capsules in the vertical position on the capsuling machine for solidification at room temperature.

The reference hard capsule is produced according to the same protocol as for capsule G6 with the proportions and the ingredients as indicated in Tables 1 and 2 above. The tablet consisting of comparative composition 1 as indicated in Table 2 is manufactured according to the usual techniques for manufacture of dosage forms of this kind.

Hard capsules G7 to G29 are produced according to the same protocol as for capsule G6 with the proportions and the ingredients as indicated in Tables 3 and 4 above.

Evaluation of Dissolution of the Active Principle of the Pharmaceutical Composition in Aqueous Medium while Passing Through the Gastrointestinal Tract In order to reproduce the effect of pH on the active principle and in particular on its dissolution during its passage through the gastrointestinal tract, a gastrointestinal environment was simulated by reproducing the pH of the stomach and then the pH of the intestine with a jump in pH. The dissolution kinetics was investigated using a simple in-vitro dissolution test with a jump in pH.

Principle:
The principle consists of determining the dissolution of the formulated active principle by studying its dissolution kinetics at 37° C., firstly in simulated gastric medium at pH 4, then in simulated intestinal medium at pH 6.5, in a time interval consistent with the gastrointestinal tract.

Equipment and Method
Equipment: precision balance (Mettler AE200 or AT261), pH meter (Knick or Schott Geräte or Inolab), thermostated Dissolutest 6 or 7 bowls (Sotax AT6 or AT7), 5 µm filter (PALL Versapore 25 mm) with syringe (Térumo), UV spectrophotometer (Gilford Response II or Perkin Elmer) or HPLC (Merck or Agilent).

Dissolution media: The simulated physiological media representative of the gastrointestinal tract are obtained from simulated gastric and intestinal fluids recommended by the USP, but used without pepsin or pancreatin.
  simulated gastric fluid—USP (without pepsin):
  2 g of sodium chloride per 900 ml of distilled water,
  pH adjusted to 1.2 with concentrated hydrochloric acid (37%),
  Q.S. 1000 ml with distilled water.
  simulated intestinal fluid—USP (without pancreatin):
  6.8 g of potassium dihydrogen phosphate per 900 ml of distilled water,
  pH adjusted to 7.5 with concentrated sodium hydroxide (10 M),
  Q.S. 1000 ml with distilled water.

The simulated gastric medium of pH 4 is thus obtained by mixing the two simulated fluids in various proportions, monitoring with a pH electrode. The dissolution medium of the intestinal type is adjusted to pH 6.5 with a few drops of concentrated soda (10M) to simulate passage of the active principle into the beginning of the intestine, without leading to dilution.

Method:

Calibration:

Standard solutions of active principle are prepared in a solvent medium, preferably in the mobile phase or ethanol or methanol, and then analyzed at the characteristic wavelength of the active principle. A calibration straight line showing the concentrations as a function of the optical densities (analysis by UV spectrophotometry) or of the areas under peak (HPLC analysis) is then determined. The equation of the straight line obtained can be used for determining the concentration of dissolved active principle from measurement of the optical density or of the area under peak.

Dissolution Kinetics:

The concentration used corresponds to the dose in 250 ml (i.e. 4 capsules in a 500-ml bowl). The dissolution kinetics is first investigated in simulated gastric medium of pH 4 in the dissolution test in bowls thermostated at 37° C., with paddle stirring at 75 rpm, for 1 hour with sampling at times 5, 15, 30, 45 and 60 minutes, then in intestinal medium with an increase in pH to 6.5 by adding a small volume of concentrated soda (example: 0.400 ml for 500 ml of medium at pH 4), monitoring with a pH electrode. The kinetics is monitored for 3 hours with sampling at times 75, 90, 120 and 180 minutes and each sample is filtered at 5 μm and then analyzed.

Analyses:

Two methods of analysis can be used depending on the sensitivity required and the dosage form under investigation: UV spectrophotometry (for active principle only) or HPLC (for active principle only or formulated).

The concentration at a time t is determined based on the previously established calibration. During analysis by UV spectrophotometry, the whole absorption spectrum is monitored at least at the end of the kinetic study. In addition, the pH of the medium is monitored at the end of the kinetic study.

Results:

The dissolution kinetics of the active principle (expressed as percentage of product released) as a function of time is plotted, first at pH 4 (simulation of the gastric medium), then at pH 6.5 (simulation of the intestinal medium) continuously on one and the same curve shown in FIG. 1. The dissolution kinetics was measured in the same conditions for the hard capsules G1-G7 and for the reference hard capsule, with the compositions defined above.

The tablet shows a significant, noticeable improvement in the percentage of active principle released relative to the reference hard capsule but only in simulated intestinal pH conditions.

Hard capsule G3 containing dronedarone hydrochloride in a matrix of lipid excipient without surfactant shows a significant improvement in the percentage of active principle released relative to the reference hard capsule or to the tablet with in addition better release in the conditions of simulated gastric pH.

Hard capsule G1 containing dronedarone hydrochloride in a matrix of lipid excipient in the presence of surfactant presents an improvement in the percentage of active principle released that is very significant relative to hard capsule G3 and relative to the reference hard capsule and the tablet.

Hard capsule G2 containing dronedarone base formed in situ in the matrix of lipid excipient from dronedarone hydrochloride shows a very significant improvement in the percentage of active principle released relative to the reference hard capsule, to the tablet and to hard capsule G3.

Hard capsules G4 and G5 containing dronedarone in the form of free base in a matrix of lipid excipient also show a very significant improvement in the percentage of active principle released relative to the reference hard capsule, to the tablet and to hard capsule G3, moreover with behavior during dissolution equivalent to that of hard capsule G2.

The beneficial effect of the presence of the lipid excipient in the formulations containing dronedarone in the base form or as hydrochloride relative to the reference hard capsule and to the tablet, in which it is not present, can be seen from the curves shown in FIG. 1.

Furthermore, it can be seen that there is a very marked improvement in the percentage of active principle released for the hard capsules that further comprise surfactant in their composition relative to the hard capsules without it (curve for G1 vs curve for G3 and curve for G5 vs curve for G6).

Moreover, in the case of the formulations containing dronedarone in its base form in the matrix, the profile of the percentage of active principle released is rapid from the very first moments in the conditions of simulated gastric pH, in contrast to the formulation containing dronedarone hydrochloride, whose release is observed in the best case at intestinal pH.

Effect of the Proportion of Gelucire 44/14 on the Base Form of Dronedarone

Figure 2:
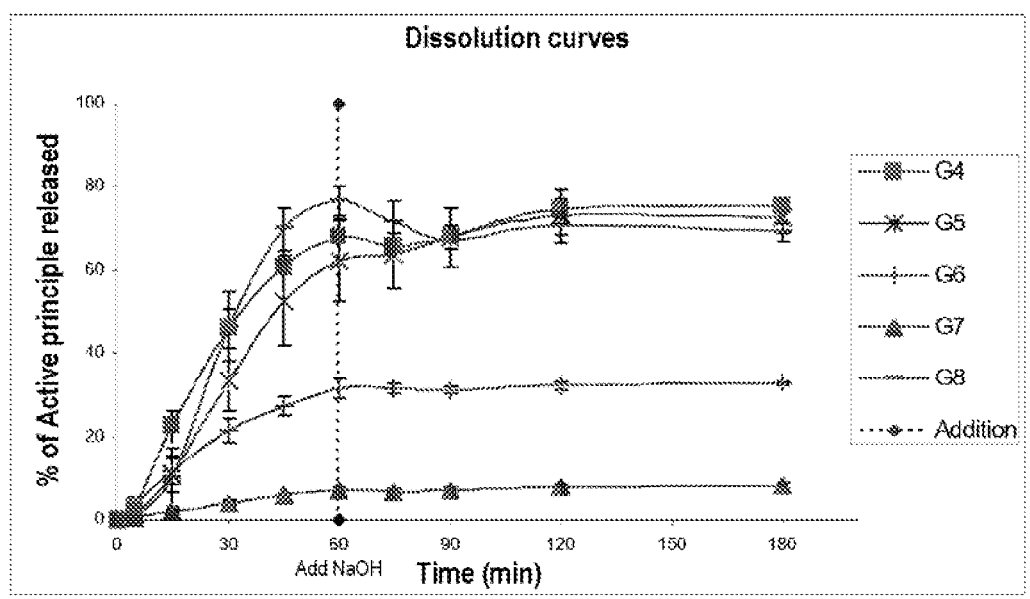
FIG. 2 shows the dissolution curves of hard capsules according to the invention (Capsules G4 to Capsules G8), all these formulations containing active principle according to the invention.

The positive effect of increasing the proportion of Gelucire can be seen from the curves shown in FIG. 2.

Figure 3:
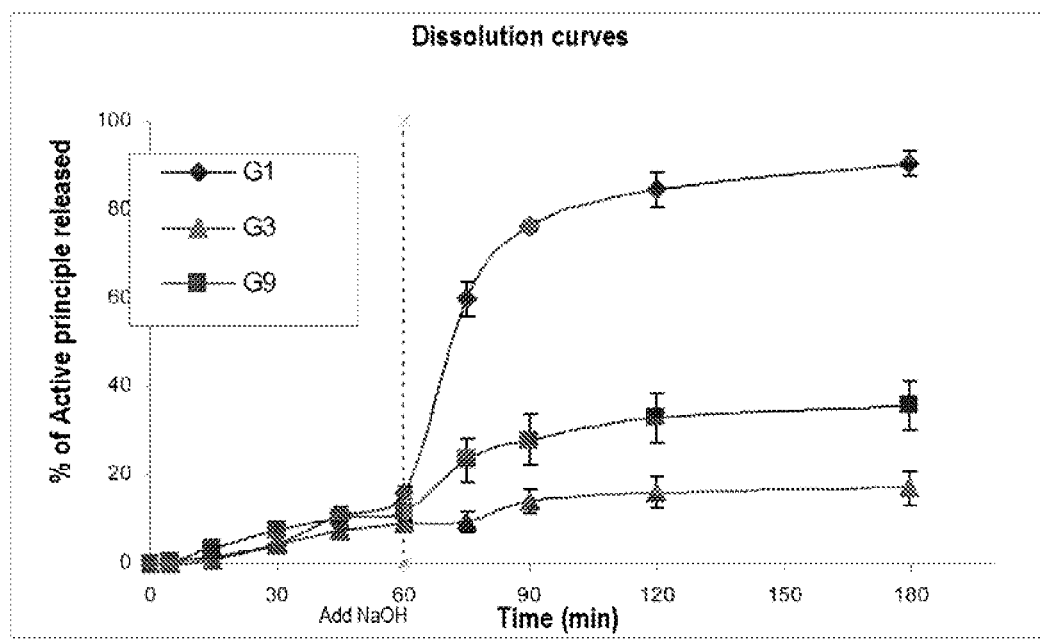
FIG. 3 shows the dissolution curves of hard capsules according to the invention (Capsules G1, G3, G9), all these formulations containing active principle according to the invention.

Effect of the Proportion of Gelucire 44/14 on the Dronedarone Hydrochloride Salt The positive effect of increasing the proportion of Gelucire can be seen from the curves shown in FIG. 3.

Effect of the Proportion of Surfactant on the Base Form of Dronedarone

Figure 4:
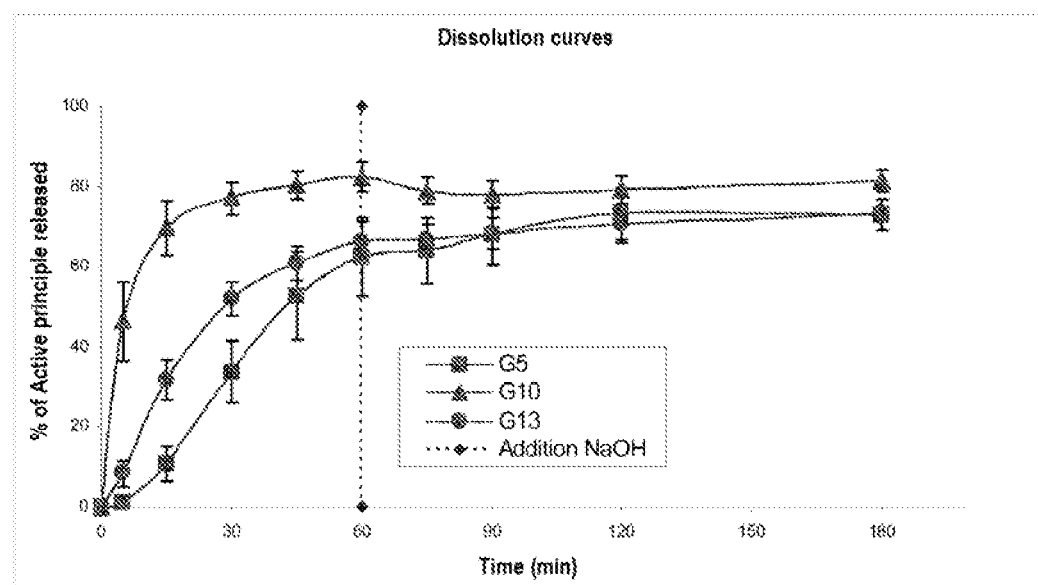
FIG. 4 shows the dissolution curves of hard capsules according to the invention (Capsules G5, G10, G13), all these formulations containing active principle according to the invention.

It can be seen from the curves shown in FIG. 4 that the proportion of surfactant in a composition according to the invention does not have an effect on the release of the active principle.

Effect of the Proportion of Surfactant on the Dronedarone Hydrochloride Salt

Figure 5:
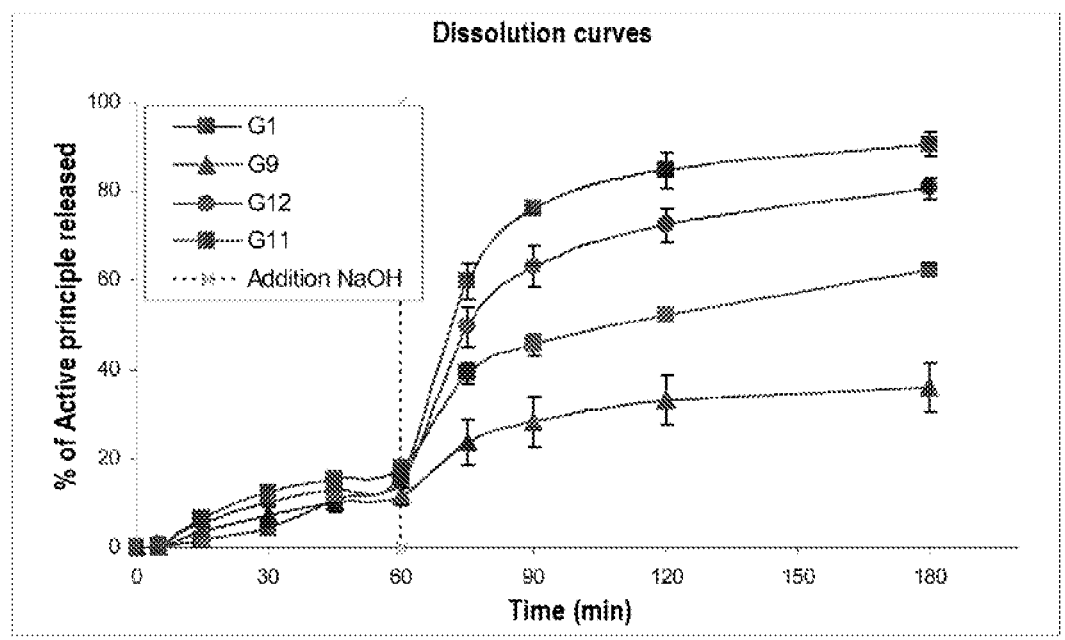
FIG. 5 shows the dissolution curves of hard capsules according to the invention (Capsules G1, G9, G11, G12), all these formulations containing active principle according to the invention.

It can be seen from the curves shown in FIG. 5 that the proportion of surfactant in a composition according to the invention has a beneficial effect on release of the active principle with an optimal proportion between 10 and 30%.

Influence of the Nature of the Surfactant on the Base Form of Dronedarone and on Dronedarone Hydrochloride

| Surfactant | HLB | % of dronedarone HCl at 180 min | % of dronedarone base form at 180 min |
| --- | --- | --- | --- |
| Pluronic L44 | 12 | 49.1 | 76.38 |
| Chrem RH40 | 14 | 59.01 | 85.3 |
| Tween 60 | 15 | 58.32 | 81.12 |
| Polox 407 | 22 | 90.49 | 72.89 |
| Polox 188 | 29 | 69.82 | 71.32 |

Figure 7:
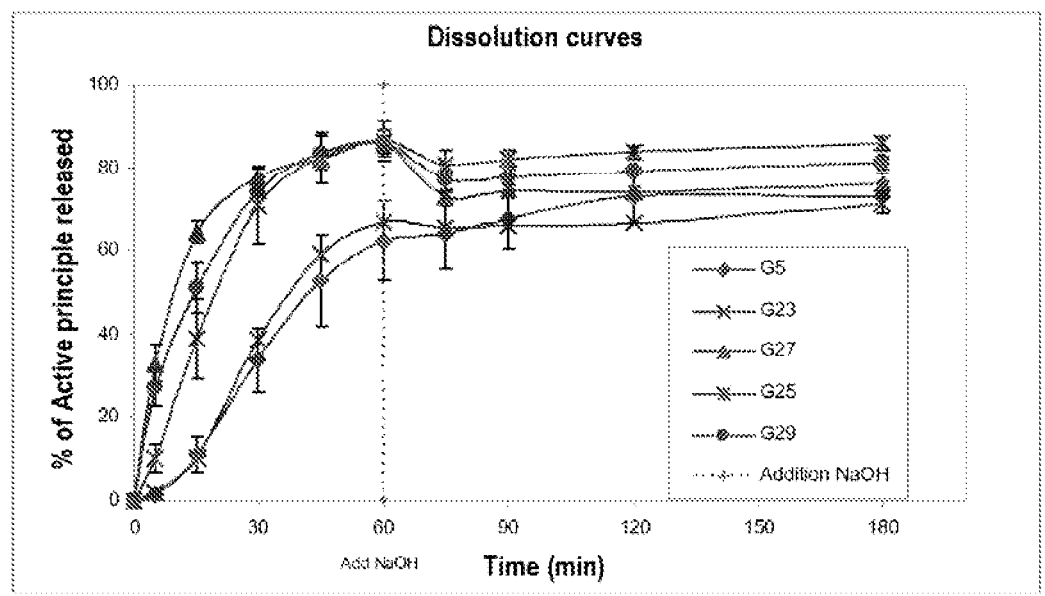
FIG. 7 shows the dissolution curves of hard capsules according to the invention (Capsules G5, G23, G25, G27, G29), all these formulations containing active principle according to the invention.

It can be seen from the curves shown in FIG. 7 that the kinetics of release of the base form are equivalent regardless of which nonionic surfactant is used.

Figure 6:
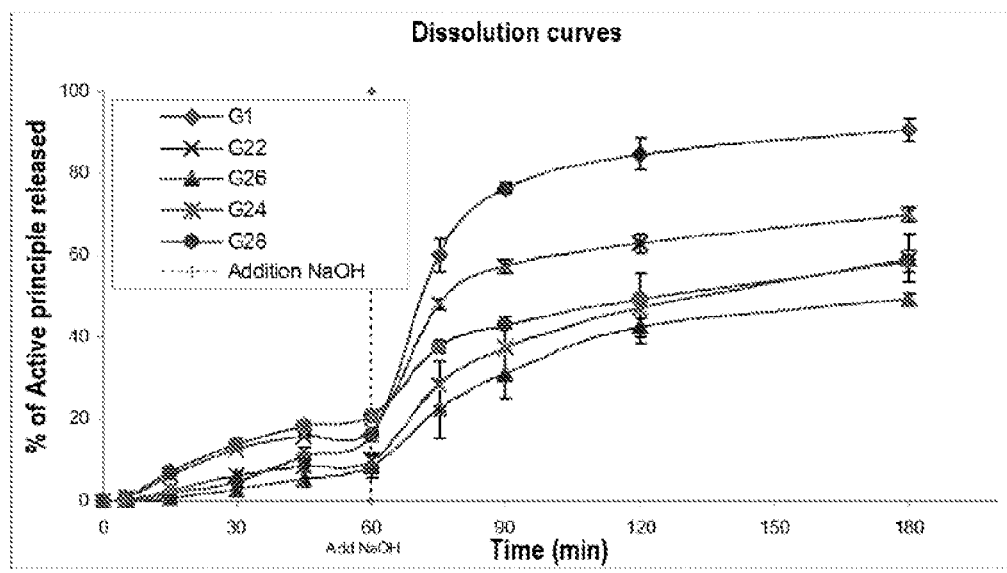
FIG. 6 shows the dissolution curves of hard capsules according to the invention (Capsules G1, G22, G24, G26, G28), all these formulations containing active principle according to the invention.

It can be seen from the curves shown in FIG. 6 that the kinetics of release of dronedarone hydrochloride have better profiles for an HLB between 15 and 25 and more particularly around 22.

Evaluation of Bioavailability

Bioavailability refers to quantification of the absorption of the medicinal product. It is related to the fraction of the dose of a medicinal product administered that reaches the general circulation and to the rate at which it reaches it. The bioavailability for oral administration depends inter alia on digestive absorption and on the first-pass metabolism in the intestine and the liver.

Protocol:

12 young subjects in good health receive, either on an empty stomach or during a high-fat meal, a single dose of 400 mg BID of dronedarone on absorbing the hard capsules G1, G2 or G3 with the compositions defined above. Blood samples are collected regularly for 48 h and the plasma collected is tested by LC-UV methods in order to determine the plasma concentration of dronedarone as a function of time. Cmax, Tmax and AUC are measured on the curves thus obtained. The results obtained are presented in Tables 4 and 5 below.

Cmax corresponds to the peak plasma concentration of dronedarone.

tmax corresponds to the time to reach Cmax.

AUC corresponds to the area under curve or integral of plasma concentration as a function of the time t.

TABLE 5

| Parameters | Hard capsule G1/reference hard capsule | Hard capsule G2/reference hard capsule | Hard capsule G3/reference hard capsule |
|---|---|---|---|
| Fasting | | | |
| $C_{max}$* | 4.57 | 8.22 | 2.57 |
| AUC** | 8.41 | 16.5 | 3.92 |
| With a meal | | | |
| $C_{max}$*** | 1.51 | 1.57 | 1.20 |
| AUC**** | 1.45 | 1.47 | 1.22 |

*Cmax (fasting) corresponds to the ratio of the Cmax measured for a hard capsule according to the invention absorbed by a fasting patient to the Cmax measured for a reference hard capsule, absorbed by this same fasting patient.
**AUC (fasting) corresponds to the ratio of the AUC measured for a hard capsule according to the invention absorbed by a fasting patient to the AUC measured for a reference hard capsule, absorbed by this same fasting patient.
***Cmax (with a meal) corresponds to the ratio of the Cmax measured for a hard capsule according to the invention absorbed by a patient during a meal to the Cmax measured for a reference hard capsule, absorbed by this same patient during a meal.
****AUC (with a meal) corresponds to the ratio of the AUC measured for a hard capsule according to the invention absorbed by a patient during a meal to the AUC measured for a reference hard capsule, absorbed by this same patient during a meal.

TABLE 6

| Parameters | Reference hard capsule (with a meal/fasting) | Hard capsule G1 (with a meal/fasting) | Hard capsule G2 (with a meal/fasting) | Hard capsule G3 (with a meal/fasting) |
|---|---|---|---|---|
| Cmax ¤ | 6.60 | 2.18 | 1.26 | 3.08 |
| Meal effect ¤¤ | 16.5 | 2.83 | 1.46 | 5.12 |

¤ Cmax corresponds to the ratio of the Cmax measured for a given hard capsule absorbed by a patient during a meal to the Cmax measured for one and the same given hard capsule absorbed by a fasting patient.
¤¤ Meal effect corresponds to the ratio of the AUC measured for a given hard capsule absorbed by a patient during a meal to the AUC measured for one and the same given hard capsule absorbed by a fasting patient.

Results:

The results indicate that in fasting conditions, the bioavailability of hard capsules G1, G2, G3 according to the invention increases significantly compared to the reference hard capsule, capsule G2 being the most effective.

Furthermore, it can be seen that the meal effect decreases significantly for the hard capsules according to the invention relative to the reference hard capsule, capsule G2 being the one with the lowest meal effect, of the order of 1.46.

Evaluation of Bioavailability

Protocol

Treatment and Administration

The dose used is 60 mg/animal regardless of the period/condition corresponding to 6 mg/kg (assuming a weight of 10 kg for a dog) and to the dose of 400 mg used in humans (i.e. about 6 mg/kg for a human weighing 70 kg).

The conditions of administration are as follows:

Period while fasting: the animals are not fed in the evening preceding dosing. Water as well as routine feed (SS-NIFFhdH) are given 1 hour and 4 hours after administration, respectively.

Period with feeding: the animals receive 50 g of a high-fat diet (SSNIFF EF Dog FDA Model high fat) 10 minutes before dosing (this diet has an energy value of 100 kcal and is composed of 15% proteins, 25% carbohydrates and 50-60% fat). Water and routine feed for dogs (SS-NIFFhdH) are then given 1 hour and 4 hours after administration, respectively.

Pretreatment with pentagastrin is carried out 0.5 h before dosing. Pentagastrin (6 µg/kg, 0.25 mL/kg) is administered intramuscularly and makes it possible to maintain the animal's gastric pH between 2-3, thus simulating the conditions in humans.

Administration of the capsule is followed by 30 mL of water by gavage, which corresponds approximately to a volume of 240 mL given to a human subject during a clinical trial.

The treatments are:

Treatment 1: 60 mg of dronedarone hydrochloride in a capsule in fasting conditions, oral route (reference hard capsule) (ref 2)

Treatment 2: 60 mg of dronedarone hydrochloride in a capsule with Gelucire and poloxamer 407, in fasting conditions, oral route (=G1).

Treatment 3: 60 mg of dronedarone base form reconstituted in situ from dronedarone hydrochloride in a capsule with Gelucire and poloxamer 407, in fasting conditions, oral route (=G2).

Treatment 4: 60 mg of dronedarone base form in a capsule with Gelucire and poloxamer 407, in fasting conditions, oral route (=G5).

Treatment 5: 60 mg of dronedarone base form in a capsule with Gelucire and poloxamer 407, in fed conditions, oral route (=G5).

Treatment 6: 60 mg of dronedarone base form in a capsule with Gelucire and without poloxamer 407, in fasting conditions, oral route (=G8).

Treatment 7: 60 mg of dronedarone base form in a capsule with Gelucire and without poloxamer 407, in fed conditions, oral route (=G8).

Samples and Analyses

The blood samples are collected in plastic tubes containing lithium heparin as anticoagulant, at the following sample collection times: before treatment and 0.5, 1, 2, 3, 4, 6, 8 and 24 hours after administration of each treatment.

The plasma concentration of dronedarone is determined using a method of exploratory analysis by liquid chromatography coupled to a mass spectrometer (LC-MS/MS). The lower limit of detection with this method for the compounds tested is 0.5 ng/mL.

Expression of the Results

The pharmacokinetic parameters are calculated from the individual concentrations by a noncompartmental analysis using the WinNonLin 5.2.1 software (Pharsight, USA) and using the theoretical sampling times (provided that the actual sampling times do not differ by more than 15% from the theoretical times).

The following pharmacokinetic parameters were measured for each treatment:

$C_{max}$ (ng/mL): corresponds to the maximum plasma concentration observed, $t_{max}$ (h): corresponds to the time observed for obtaining the maximum concentration, $AUC_{last}$: corresponds to the area under curve or integral of the plasma concentration as a function of the time t calculated by the trapezium method from $t_0$ up to the time corresponding to the last quantifiable concentration.

AUC: corresponds to the area under curve or integral of plasma concentration as a function of time extrapolated to infinity.

T1/2z; terminal elimination half-life

The following parameters were also evaluated:
relative bioavailability on Cmax and AUC
ratio of the meal effect on Cmax and AUC.

Results

TABLE 7

| Pharmacokinetic parameters of dronedarone (Mean ± SD (CV %)) in group 1 (n = 4 per formulation) | | | | | |
|---|---|---|---|---|---|
| Treatment | $C_{max}$ (ng/mL) | $t_{max}$ (h)* | $AUC_{last}$ (ng · h/mL) | AUC (ng · h/mL) | $T_{1/2z}$ (h) |
| reference capsule with dronedarone HCl and poloxamer, fasting | 5.73 ± 4.57 (80%) | 2.50 (0.50-3.00) | 18.9 ± 14.2 (75%) | 21.2 ± 14.4 (68%) | 1.88 ± 0.624 (33%) |
| Capsule with Gelucire, dronedarone HCl and with poloxamer, fasting | 13.5 ± 4.87 (36%) | 1.50 (0.50-2.00) | 45.0 ± 17.8 (40%) | 51.3 ± 21.2 (41%) | 2.53 ± 0.377 (15%) |
| capsule with Gelucire, dronedarone base form reconstituted and poloxamer, fasting | 19.5 ± 13.0 (67%) | 1.00 (0.50-1.00) | 53.3 ± 33.4 (63%) | 60.5 ± 35.7 (59%) | 2.70 ± 0.762 (28%) |

*median (min-max)

TABLE 8

| Pharmacokinetic parameters of dronedarone (Mean ± SD (CV %)) in group 2 (n = 4 per formulation) | | | | | |
|---|---|---|---|---|---|
| Treatment | $C_{max}$ (ng/mL) | $t_{max}$ (h)* | $AUC_{last}$ (ng · h/mL) | AUC (ng · h/mL) | $T_{1/2z}$ (h) |
| reference capsule with dronedarone HCl and poloxamer, fasting | 7.36 ± 4.83 (66%) | 1.00 (0.50-2.00) | 21.5 ± 13.9 (65%) | 28.1 ± 18.0 (64%)* | 3.07 ± 0.153 (5%)* |
| capsule with Gelucire, dronedarone base form and poloxamer, fasting | 24.6 ± 14.8 (60%) | 1.00 (1.00-2.00) | 62.3 ± 34.0 (55%) | 69.0 ± 37.7 (55%) | 2.40 ± 0.535 (22%) |
| capsule with Gelucire, dronedarone base form and poloxamer, fed | 16.9 ± 7.41 (44%) | 1.00 (1.00-2.00) | 44.0 ± 19.9 (45%) | 48.0 ± 21.5 (45%) | 2.10 ± 0.183 (9%) | n = 3; * median (min-max)

TABLE 9

| Treatment | $C_{max}$ (ng/mL) | $t_{max}$ (h)* | $AUC_{last}$ (ng · h/mL) | AUC (ng · h/mL) | $T_{1/2z}$ (h) |
|---|---|---|---|---|---|
| reference capsule with dronedarone HCl and poloxamer, fasting | 4.52 ± 3.04 (67%) | 1.50 (0.50-6.00) | 15.3 ± 8.62 (56%) | 15.6 ± 7.73 (50%) | 2.90 ± 0.794 (27%) |
| capsule with Gelucire, dronedarone base form without poloxamer, fasting | 15.6 ± 4.99 (32%) | 1.00 (1.00-2.00) | 57.5 ± 11.3 (20%) | 66.8 ± 10.1 (15%) | 2.68 ± 0.377 (14%) |

TABLE 9-continued

| Treatment | $C_{max}$ (ng/mL) | $t_{max}$ (h)* | $AUC_{last}$ (ng·h/mL) | AUC (ng·h/mL) | $T_{1/2z}$ (h) |
|---|---|---|---|---|---|
| capsule with Gelucire, dronedarone base form without poloxamer, fed | 30.7 ± 12.7 (41%) | 1.00 (0.50-2.00) | 82.8 ± 29.1 (35%) | 91.8 ± 31.5(34%) | 2.53 ± 0.171 (7%) |

*median (min-max)
All the dogs receiving the reference formulation have similar exposure in fasting conditions regardless of the group.

TABLE 10

Relative bioavailability of dronedarone (%) with 90% CI in fasting conditions (using the capsule as reference)

| Treatment | $C_{max}$ | $AUC_{last}$ | AUC |
|---|---|---|---|
| capsule with Gelucire, dronedarone HCl with poloxamer, fasting | 274 (120-625) | 283 (112-716) | 271 (119-613) |
| capsule with Gelucire base reconstituted with poloxamer, fasting | 357(157-812) | 311 (123-785) | 301 (133-682) |
| Capsule with Gelucire and dronedarone base form with poloxamer, fasting | 339 (159-724) | 325 (177-595) | 248 (134-459)* |
| Capsule with Gelucire and dronedarone base form without poloxamer, fasting | 401 (230-700) | 432 (240-778) | 500 (273-915) | n = 3 for 2B1

All the formulations tested display a higher bioavailability than the reference capsule with a relative bioavailability in the range from 271% to 500% in fasting conditions.

The formulations with Gelucire with dronedarone hydrochloride and reconstituting the base in situ (Frel=301%) showed a higher bioavailability than the reference capsule, as in the clinical test described above.

The formulations with Gelucire using the native base display a relative bioavailability similar to the Gelucire formulation using dronedarone hydrochloride and reconstituting the base in situ when compared with the reference in fasting conditions as indicated by the coverage of the confidence interval.

The formulations with Gelucire with or without poloxamer show a similar relative bioavailability with a bioavailability higher by 3 to 5 compared to the reference capsule.

TABLE 11

Ratio of the meal effect for the capsule with Gelucire, dronedarone base form with poloxamer

| Treatment | $C_{max}$ | $AUC_{last}$ | AUC |
|---|---|---|---|
| fed/fasting | 0.73 (0.35-1.53) | 0.71 (0.41-1.23) | 0.70 (0.41-1.21) |

There is a tendency for a slight decrease in Cmax of 1.4 times when the Gelucire capsule with poloxamer is administered with high-fat feed. This decrease is not significant as the 90% CI includes unity.

TABLE 12

Ratio of the meal effect for the capsule with Gelucire, dronedarone base form without poloxamer

| Treatment | $C_{max}$ | $AUC_{last}$ | AUC |
|---|---|---|---|
| fed/fasting | 1.93(1.16-3.21) | 1.39 (0.82-2.35) | 1.32 (0.81-2.16) |

There is a tendency for a positive meal effect when the Gelucire capsule without poloxamer is administered with high-fat feed. In fact Cmax is increased by 1.9 times, $AUC_{last}$ by 1.4 times and AUC by 1.3 times. However, this increase is not significant regarding the AUC as the 90% CI includes unity.

What is claimed is:

1. A pharmaceutical composition comprising 20-40 wt % of at least one active principle selected from (i) 2-n-butyl-3-[4-(3-di-n-butylaminopropoxy)benzoyl]-5-methylsulfonamidobenzofuran in the form of base and (ii) 2-n-butyl-3-[4-(3-di-n-butylaminopropoxy)benzoyl]-5-methylsulfonamidobenzofuran in the form of a pharmaceutically acceptable salt; and 50-60 wt % of at least one amphiphilic lipid excipient with HLB value between 2 and 20 selected from the semi-solid substituted glycerides, the liquid substituted glycerides, the semi-solid substituted polyoxylglycerides, the liquid substituted polyoxylglycerides and mixtures thereof;
wherein the percentages are expressed by weight relative to the total weight of said composition.

2. The composition according to claim 1, wherein the 2-n-butyl-3-[4-(3-di-n-butylaminopropoxy)benzoyl]-5-methylsulfonamidobenzofuran in the form of a pharmaceutically acceptable salt is selected from 2-n-butyl-3-[4-(3-di-n-butylaminopropoxy)benzoyl]-5-methylsulfonamidobenzofuran hydrochloride, 2-n-butyl-3-[4-(3-di-n-butylaminopropoxy)benzoyl]-5-methylsulfonamidobenzofuran fumarate and 2-n-butyl-3-[4-(3-di-n-butylaminopropoxy)benzoyl]-5-methylsulfonamidobenzofuran oxalate.

3. The composition according to claim 1, wherein the active principle is selected from 2-n-butyl-3-[4-(3-di-n-butylaminopropoxy)benzoyl]-5-methylsulfonamidobenzofuran in the form of base and 2-n-butyl-3-[4-(3-di-n-butylaminopropoxy)benzoyl]-5-methylsulfonamidobenzofuran hydrochloride.

4. The composition according to claim 1, wherein said composition further comprises at least one surfactant and/or at least one co-solvent.

5. The composition according to claim 1, wherein said amphiphilic lipid excipient with HLB value between 2 and 20 has a melting point below 50° C.

6. The composition according to claim 1, wherein said lipid excipient is selected from the medium-chain mono- and diglycerides, propylene glycol monolaurate, caprylocaproyl macrogol-8 glycerides, propylene glycol caprylic acid monoester and mixtures thereof.

7. The composition according to claim 1, wherein said lipid excipient is selected from the lipid excipients having an HLB value between 5 and 18.

8. The composition according to claim 1, comprising 2-n-butyl-3-[4-(3-di-n-butylaminopropoxy)benzoyl]-5-methyl-sulfonamidobenzofuran hydrochloride, as active principle and/or at least one semi-solid substituted polyoxylglyceride as lipid excipient.

9. The composition according to claim 1, comprising up to 30%:
    of at least one compound selected from surfactants, co-solvents, diluents, disintegrants, lubricants, organic or inorganic bases and plasticizers,
the percentages being expressed by weight relative to the total weight of said composition.

10. The composition according to claim 1, comprising 0.1-30% wt. of at least one surfactant, and 0.1-29% wt. of at least one co-solvent:
the percentages being expressed by weight relative to the total weight of said composition.

11. The composition according to claim 10, comprising:
    1-20 wt % of at least one surfactant; and
    1-20 wt % of at least one co-solvent.

12. The composition according to claim 11, comprising:
    5-15 wt % of at least one surfactant; and
    2-15 wt % of at least one co-solvent.

13. The composition according to claim 10, wherein the surfactant is hydrophilic and nonionic.

14. The composition according to claim 10, wherein the surfactant is selected from:
    ethylene oxide/propylene oxide copolymers;
    polyethoxylated castor oils;
    ethoxylated polysorbates, and
    polyethylene hydroxystearates.

15. The composition according to claim 10, wherein the surfactant is poloxamer 407.

16. The composition according to claim 10, wherein the co-solvent is selected from the alcoholic organic solvents and the glycol derivatives.

17. A dosage form comprising a composition according to claim 1.

18. The dosage form according to claim 17, which is in the form of a capsule selected from hard capsules, soft shell capsules, enteric capsules and modified-release capsules.

19. The dosage form according to claim 18, which is in the form of a hard capsule.

20. The dosage form according to claim 17, comprising between 50 and 500 mg of active principle.

21. The dosage form according to claim 17, comprising between 200 and 400 mg of active principle.

* * * * *

UNITED STATES PATENT AND TRADEMARK OFFICE
CERTIFICATE OF CORRECTION

Page 1 of 1

PATENT NO. : 9,018,250 B2
APPLICATION NO. : 13/887562
DATED : April 28, 2015
INVENTOR(S) : Bernard Abramovici et al.

It is certified that error appears in the above-identified patent and that said Letters Patent is hereby corrected as shown below:

In the Claims

In column 26, line 67, in claim 6, delete "from the" and insert -- from --, therefor.

In column 27, lines 20-21, in claim 10, delete "comprising 0.1-30%" and insert -- comprising: 0.1-30% --, therefor.

In column 27, line 22, in claim 10, delete "co-solvent:" and insert -- co-solvent; --, therefor.

Signed and Sealed this
Twenty-second Day of December, 2015

Michelle K. Lee
*Director of the United States Patent and Trademark Office*